United States Patent
Verkruijsse et al.

(10) Patent No.: US 10,893,814 B2
(45) Date of Patent: Jan. 19, 2021

(54) SYSTEM AND METHOD FOR OBTAINING VITAL SIGN RELATED INFORMATION OF A LIVING BEING

(71) Applicant: KONINKLIJKE PHILIPS N.V., Eindhoven (NL)

(72) Inventors: Willem Verkruijsse, Veldhoven (NL); Gerard De Haan, Helmond (NL); Andreas Wolfgang Schlack, Boeblingen (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1142 days.

(21) Appl. No.: 15/285,559

(22) Filed: Oct. 5, 2016

(65) Prior Publication Data

US 2017/0095170 A1  Apr. 6, 2017

Related U.S. Application Data

(60) Provisional application No. 62/237,737, filed on Oct. 6, 2015.

(51) Int. Cl.
*A61B 5/00* (2006.01)
*A61B 5/11* (2006.01)
(Continued)

(52) U.S. Cl.
CPC ........ *A61B 5/02416* (2013.01); *A61B 5/0064* (2013.01); *A61B 5/0077* (2013.01);
(Continued)

(58) Field of Classification Search
CPC . A61B 5/02416; A61B 5/0077; A61B 5/0064; A61B 5/021; A61B 5/01;
(Continued)

(56) References Cited

U.S. PATENT DOCUMENTS

| 4,218,144 A * | 8/1980 | Whitehouse ......... G01B 11/303 |
| | | 250/208.2 |
| 9,787,965 B2 | 10/2017 | Tozuka |

(Continued)

FOREIGN PATENT DOCUMENTS

| EP | 2223650 | 1/2010 |
| EP | 2380493 | 10/2011 |
| WO | 2009/115947 | 9/2009 |
| WO | 2012/143842 | 10/2012 |
| WO | 2013/186696 | 12/2013 |
| WO | 2014/066791 | 5/2014 |

(Continued)

OTHER PUBLICATIONS

Wim Verkruysse, Lars O. Svaasand, and J. Stuart Nelson, "Remote plethysmographic imaging using ambient light", Optics Express, vol. 16, No. 26, Dec. 2008.

*Primary Examiner* — Boniface N Nganga (57) ABSTRACT

The present invention relates to a device, system and method for obtaining vital sign related information of a living being. The proposed device comprises an input unit for receiving an input signal generated from light received in at least one wavelength interval reflected from a skin region of a living being, said input signal representing vital sign related information from which a vital sign of the living being can be derived, a processing unit for processing the input signal and deriving vital sign related information of said living being from said input signal, an orientation estimation unit for estimating the orientation of said skin region, and a control unit for controlling an illumination unit for illuminating said skin region with light to illuminate said skin region based on the estimated orientation of said skin region and/or for controlling said processing unit to derive vital sign related information from said input signal obtained during time intervals selected based on the estimated orientation of said skin region.

19 Claims, 6 Drawing Sheets

(51) Int. Cl.
 *A61B 5/024* (2006.01)
 *A61B 5/08* (2006.01)
 *A61B 5/01* (2006.01)
 *A61B 5/021* (2006.01)
 *A61B 5/113* (2006.01)

(52) U.S. Cl.
 CPC ................ *A61B 5/01* (2013.01); *A61B 5/021* (2013.01); *A61B 5/02405* (2013.01); *A61B 5/0816* (2013.01); *A61B 5/7278* (2013.01); *A61B 5/113* (2013.01); *A61B 5/1121* (2013.01); *A61B 5/7203* (2013.01)

(58) Field of Classification Search
 CPC . A61B 5/0816; A61B 5/02405; A61B 5/7278; A61B 5/7203; A61B 5/1121; A61B 5/113
 See application file for complete search history.

(56) References Cited

U.S. PATENT DOCUMENTS

| | | |
|---|---|---|
| 2009/0275841 A1 | 11/2009 | Melendez |
| 2009/0306498 A1 | 12/2009 | Bodduluri et al. |
| 2009/0315989 A1 | 12/2009 | Adelson |
| 2011/0096150 A1 | 4/2011 | Wadman |
| 2011/0304705 A1 | 12/2011 | Kantor |
| 2013/0035599 A1 | 2/2013 | De Bruijn |
| 2014/0221728 A1 | 8/2014 | Bodlaender |
| 2014/0253709 A1 | 9/2014 | Bresch |
| 2014/0276088 A1* | 9/2014 | Drucker ............... A61B 5/0082 600/473 |

FOREIGN PATENT DOCUMENTS

| | | | |
|---|---|---|---|
| WO | 2014/087310 | 6/2014 | |
| WO | WO-2014087310 A1 * | 6/2014 | ........... A61B 5/0077 |

* cited by examiner

SYSTEM AND METHOD FOR OBTAINING VITAL SIGN RELATED INFORMATION OF A LIVING BEING

CROSS REFERENCE TO RELATED APPLICATIONS

This application claims the benefit of U.S. Provisional Application No. 62/237,737 filed Oct. 6, 2015, and European Patent Application Number 15188480.6 filed Oct. 6, 2015, which is incorporated herein by reference.

FIELD OF THE INVENTION

The present invention relates to a device, a system and a corresponding method for obtaining vital sign related information of a living being.

BACKGROUND OF THE INVENTION

Unobtrusive vital sign monitoring using a video camera, or remote PPG (photoplethysmography), has been demonstrated and found relevant for patient monitoring. Remote photoplethysmographic imaging is, for instance, described in Wim Verkruysse, Lars O. Svaasand, and J. Stuart Nelson, "Remote plethysmographic imaging using ambient light", Optics Express, Vol. 16, No. 26, December 2008. It is based on the principle that temporal variations in blood volume in the skin lead to variations in light absorptions by the skin. Such variations can be registered by a video camera that takes images of a skin area, e.g. the face, while processing calculates the pixel average over a selected region (typically part of the cheek in this system). By looking at periodic variations of this average signal, the heart beat rate and respiratory rate can be extracted. There are meanwhile a number of further publications and patent applications that describe details of devices, systems and methods for obtaining vital signs of a patient by use of remote PPG.

Thus, the pulsation of arterial blood causes changes in light absorption. Those changes observed with a photodetector (or an array of photodetectors) form a PPG (photoplethysmography) signal (also called, among other, a pleth wave). Pulsation of the blood is caused by the beating heart, i.e. peaks in the PPG signal correspond to the individual beats of the heart. Therefore, a PPG signal is a heartbeat signal in itself. The normalized amplitude of this signal is different for different wavelengths, and for some wavelengths it is also a function of blood oxygenation.

Although regular video data have been shown to yield adequate vital signs (sometimes also called biometrical signals, such as heartbeat, respiration rate, SpO2 rate, etc.) in many cases, the image acquisition for challenging cases, like strong motion, low light levels, non-white illumination, needs further improvement. The known methods, systems and devices are generally robust to motion and different lighting environments as long as one dominant light source is present. In such condition the PPG technology has proven to be accurate and robust up to a point that it can be used, at least for some vital signs like heart rate, on a treadmill during fitness exercises.

One major problem encountered in image-based (e.g. camera-based) vital signs monitoring occurs when no dominant light is present in the environment. Further, a particular illumination is not always optimal for all measurements, e.g. for different skin types, body postures or after body movements.

WO 2014/087310 A1 discloses a device and method for obtaining vital sign information of a living being. The disclosed device comprises a detection unit for receiving light in at least one wavelength interval reflected from at least a region of interest of a living being and for generating an input signal from the received light, a processing unit for processing the input signal and deriving vital sign information of said living being from said input signal by use of remote photoplethysmography, an illumination unit for illuminating at least said region of interest with light, and a control unit for controlling said illumination unit based on said input signal and/or said derived vital sign information. However, further improvement of motion robustness is desired.

WO 2013/186696 A1 discloses a system for determining a vital sign of a subject, comprising an imaging unit for obtaining video data of the subject, a marker directly or indirectly attached to a body of the subject, wherein the marker comprises a graphical pattern, an image processing unit for detecting said marker in said video data, and an analysis unit adapted to extract a vital sign parameter related to the vital sign of the subject from said video data and to determine the vital sign from said vital sign parameter.

SUMMARY OF THE INVENTION

It is an object of the present invention to provide a device, a system and a corresponding method for obtaining vital sign related information of a living being providing a higher motion robustness with respect to motion of the living being.

In a first aspect of the present invention a device for obtaining vital sign related information of a living being is presented comprising:

an input unit configured to receive an input signal generated from light received in at least one wavelength interval reflected from a skin region of a living, said input signal representing vital sign related information from which a vital sign of the living being can be derived, a processing unit configured to process the input signal and to derive vital sign related information of said living being from said input signal, an orientation estimation unit configured to estimate the orientation of said skin region, and a control unit configured to control an illumination unit configured to illuminate said skin region with light to illuminate said skin region based on the estimated orientation of said skin region and/or to control said processing unit to derive vital sign related information from said input signal during time intervals selected based on the estimated orientation of said skin region.

In a further aspect of the present invention a corresponding method for obtaining vital sign information of a living being is presented.

In another aspect of the present invention a system for obtaining vital sign related information of a living being is presented, said system comprising:

a detection unit configured to receive light in at least one wavelength interval reflected from a skin region of a living being and to generate an input signal from the received light representing vital sign related information from which a vital sign of the living being can be derived, an illumination unit configured to illuminate said skin region with light, and a device as claimed in claim 1 for obtaining vital sign related information of a living being from said input signal.

In a yet further aspects of the present invention, there are provided a computer program which comprises program code means for causing a computer to perform the steps of the method disclosed herein when said computer program is carried out on a computer, as well as a non-transitory computer-readable recording medium that stores therein a computer program product, which, when executed by a processor, causes the method disclosed herein to be performed.

Preferred embodiments of the invention are defined in the dependent claims. It shall be understood that the claimed system, method, computer program and medium have similar and/or identical preferred embodiments as the claimed device and as defined in the dependent claims.

According to the present invention it has been found that even with perfect motion tracking (e.g. following motion in the image plane, in particular motion of the skin region), changes in orientation of the skin (due to respiration, heart rate or other subject movements) with respect to the illumination can significantly impact the quality of the acquired input signal or of a PPG signal derived from said input signal, particularly if the illumination onto the skin is at a large angle with the skin surface-normal. This is because the projected light energy is distributed over a surface that depends on the angle between skin surface-normal and illumination angle.

For illumination from a certain solid angle, the irradiated surface is bigger when the angle between the surface-normal and the incident light (in particular the incident main ray of light) increases. Hence, the irradiance ($W/m^2$) decreases with increasing angle. Rather than following algorithmic approaches, which can to some extent clean up raw signals, according to the present invention, cleaner raw signals (input signals) are acquired. This is achieved by controlling the illumination of the skin region (also called region of interest) based on the estimated orientation of the skin region, e.g. with respect to the illumination or to a known reference plane, so that the skin region gets illuminated in an optimized way with respect to the acquisition of information, from which one or more accurate vital signs can be derived in a robust manner. The control is preferably performed such that the illumination is done at angles at which changes in skin orientation have a minimal impact on the irradiated, and consequently also the reflected, light intensity.

For the purpose of deriving vital sign related information of said living being from said input signal by use of photoplethysmography a corresponding processing unit for processing the input signal is provided. This provides that as an alternative to the illumination control, light from different illumination angles can e.g. be time-multiplexed, and said processing unit may decide which time interval(s) to use for processing and, optionally, vital sign extraction.

Generally, the interaction of electromagnetic radiation, in particular light, with biological tissue is complex and includes the (optical) processes of (multiple) scattering, backscattering, absorption, transmission and (diffuse) reflection. The term "reflect" as used in the context of the present invention is not to be construed as limited to specular reflection but comprises the afore-mentioned types of interaction of electromagnetic radiation, in particular light, with tissue and any combinations thereof.

The term "vital sign" as used in the context of the present invention refers to a physiological parameter of a subject (herein also called living being or person or patient) and derivative parameters. In particular, the term "vital sign" comprises blood volume pulse-signal, heart rate (HR) (sometimes also called pulse rate), heart rate variability (pulse rate variability), pulsatility strength, perfusion, perfusion indicator, perfusion variability, Traube Hering Mayer waves, respiratory rate (RR), skin temperature, blood pressure, a concentration of a substance in blood and/or tissue, such as (arterial) blood oxygen saturation or glucose level. Furthermore, "vital sign" generally includes health indications obtained from the shape of the PPG signal (e.g. shape may say something about partial arterial blockage (e.g. shape obtained from PPG signals of the hand gets more sinusoidal when applying a blood-pressure cuff on the arm), or about the skin thickness (e.g. a PPG signal from the face is different than from the hand), or maybe even about the temperature, etc.).

The term "vital sign information" as used in the context of the present invention comprises the one or more measured vital signs as defined above. Furthermore, it comprises data referring to a physiological parameter, corresponding waveform traces or data referring to a physiological parameter of a time that can serve for subsequent analysis.

For obtaining a vital sign information signal of the subject the data signals of skin pixel areas within the skin area are evaluated. Here, a "skin pixel area" means an area comprising one skin pixel or a group of adjacent skin pixels, i.e. a data signal may be derived for a single pixel or a group of skin pixels.

According to the present invention various alternatives are described to estimate the skin surface orientation, to determine the best control of the illumination unit, in particular the illumination angles, in an automated fashion and to provide recipes to adapt the illumination to these estimates for optimal signal quality.

In one embodiment said control unit is configured to control the intensity, direction, distribution, and/or illumination angle of at least part of the light emitted by said illumination unit. Dependent on the estimated orientation of the skin region and the design of the illumination unit the corresponding (optimal) parameter of the illumination unit can thus be appropriately controlled. Of course, other (additional or alternative) parameters may be used for the control, such as the uniformity of illumination in the ROI, good/stable illumination in all relevant channels (wavelengths), no shadow in the ROI, etc. Further, in an embodiment only particular wavelengths are modified (e.g. the wavelength used for vital signs extraction) whereas other wavelengths (e.g. for orientation measurement) remain unaffected.

In another embodiment said orientation estimation unit is configured to estimate the orientation of the surface-normal of said skin region, and said control unit is configured to control the intensity, direction, distribution, and/or illumination angle of at least part of the light emitted by said illumination unit such that most or all light is emitted from an illumination angle closest or identical to the estimated surface-normal. Hence, this embodiment minimizes the amplitude of the variation in irradiance by illuminating the skin region at an angle substantially perpendicular to the average skin orientation of a region of interest (ROI), or at least prevents large angles, e.g. larger than 45 degrees. This reduces the variance in irradiance (noise) due to subject movements and thus leads to more robust and accurate input signals and, consequently, vital signs derived therefrom.

In another embodiment said orientation estimation unit is configured to regularly or continuously estimate the orientation of said skin region and wherein said control unit is configured to adjust the control of the illumination unit accordingly. In this way, movements of the subject can be quickly or even immediately recognized so that the illumination can be adapted accordingly in an automated manner.

While according to one option of the present invention the control unit controls the illumination unit based on the estimated orientation of the skin region, according to an alternative (or additional) option it controls the processing unit to derive vital sign related information based on the estimated orientation of said skin region. In an embodiment of this option the control unit is configured to control said illumination unit to illuminate said skin region in subsequent time intervals from different illumination angles and to control said processing unit to derive vital sign related information from said input signal obtained during time intervals selected based on the estimated orientation of said skin region. Hence, the illumination is e.g. time multiplexed and only the processing is controlled to use only input signals acquired at certain time intervals at which the illumination has be made from the best illumination angle.

Generally the use of one illumination element as illumination unit is sufficient (whose position and/or orientation with respect to the skin region may be changeable), but preferably said illumination unit comprises two or more illumination elements (also called light sources), e.g. a plurality of LEDs. Thus, e.g. by individually controlling the separate illumination elements the desired control of the illumination can be achieved in a fast, simple and flexible manner. For this purpose, said two or more illumination elements are preferably arranged at different locations and/or with different orientations for illuminating a skin region from different illumination angles. Said two or more illumination elements are preferably controlled individually and may e.g. be LEDs, laser diodes, conventional light bulbs, neon lights, etc. which can be controlled.

The control unit is preferably configured to individually control said illumination elements, in particularly to individually control the intensity of the illumination elements. This allows, for instance, to increase the power of the illumination elements that illuminate the skin region at an angle closest to the surface-normal and to decrease the power of the illumination elements that illuminate the skin region at larger angle(s).

For estimating the orientation of the skin region in an accurate and reliable manner various embodiment exists. In one embodiment said control unit is configured to control said illumination elements to illuminate said skin region in a multiplexed and/or modulated manner, said detection unit is configured to subsequently receive light reflected from said skin region in response to said subsequent illuminations and to generate reflection signals from the received light, said orientation estimation unit is configured to determine the reflection signal with the highest intensity. Said control unit is further configured to control said illumination unit such that the illumination element, whose illumination resulted in the reflection signal with the highest intensity, illuminates said skin region exclusively or with the highest intensity among all illumination elements and/or to control said processing unit to derive vital sign related information from said input signal obtained during time intervals, during which the illumination element, whose illumination resulted in the reflection signal with the highest intensity, illuminates said skin region exclusively or with the highest intensity among all illumination elements.

In another embodiment the illumination unit (comprising one or more illumination elements) emits a spectrum comprising a wavelength used for orientation and wavelength used for vital signs measurement. In such an embodiment the spectrum of the illumination unit may be changed, i.e. only the intensity of the wavelength used for vital sign measurement may be adapted, while optionally the wavelength used for orientation measurement may be kept at the same level. This provides the advantage that the orientation measurement is not suffering from reduced intensity in some directions.

In an alternative embodiment said control unit is configured to control said illumination elements to pairwise illuminate said skin region, wherein different pairs of neighboring illumination elements alternately illuminate said skin region with different alternation frequencies, with different wavelengths, at different times and/or with a synchronized flickering, said detection unit is configured to subsequently receive light reflected from said skin region in response to said alternate illuminations and to generate reflection signals from the received light, said orientation estimation unit is configured to determine the reflection signal with the smallest intensity modulation. Said control unit is further configured to control said illumination unit such that the pair of illumination elements, whose illumination resulted in the reflection signal with the smallest intensity modulation, illuminates said skin region exclusively or with the highest intensity among all illumination elements or such that only illumination in time slots with illumination that resulted in the reflection signal with the smallest intensity modulation is used for illumination of said skin region or such that only illumination in time slots with illumination that resulted in the reflection signal with the smallest intensity modulation is used for illumination of said skin region and/or to control said processing unit to derive vital sign related information from said input signal obtained during time intervals, during which the pair of illumination elements, whose illumination resulted in the reflection signal with the smallest intensity modulation, illuminates said skin region exclusively or with the highest intensity among all illumination elements.

In a further embodiment said detection unit comprises a camera for generating said input signal from light received by the camera and a photodiode for generating said reflection signals from light received by the photodiode, wherein said illumination unit comprises a first set of illumination elements for illuminating said skin region to enable the generation of input signals by said camera and a second set of illumination elements for illuminating said skin region to enable the generation of reflection signals by said photodiode. From the input signals the vital sign information is then derived, whereas from the reflection signals the orientation of the skin region is estimated. The photodiode allows higher modulation frequencies so that the light reflected from the skin may be focused to a larger extent.

Further, the illumination elements of said second set are configured to illuminate said skin region with light of a wavelength or wavelength range outside the sensitivity interval of said camera so that orientation estimation and acquisition of light for the generation of input signals can be done simultaneously with disturbing each other.

The orientation estimation unit may be configured to process distance data, in data, in particular time-of-flight (TOF) data as e.g. acquired by a TOF camera or a radar unit, and to determine a 3D model of the skin surface including said skin region. This provides another simple option to estimate the orientation of the skin region in a rather precise manner.

While generally the use of one detection element as detection unit is sufficient, said detection unit preferably comprises two or more detection elements. Said detection elements are, for instance, image sensors, video camera, RGB camera, infrared camera or still image cameras. While the detection elements generally have identical parameters but are located at different positions and/or with different orientations, in an embodiment the detection elements are different and/or have different parameters so that the detection element resulting in the best vital sign information can be selected for signal evaluation. In still another embodiment the input signals from two or more detection elements may be commonly evaluated, e.g. after averaging the input signals.

In a further aspect the present invention presents a system for obtaining vital sign related information of a living being, said system comprising a processor configured to carry out the steps of:

illuminating at least a skin region of a living being with light, receiving light in at least one wavelength interval reflected from said skin region, generating an input signal from the received light representing vital sign related information from which a vital sign of the living being can be derived, processing the input signal and deriving vital sign information of said living being from said input signal, estimating the orientation of said skin region, and controlling said illumination based on the estimated orientation of said skin region to illuminate said skin region and/or said processing to derive vital sign related information based on the estimated orientation of said skin region.

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE INVENTION

Figure 1:
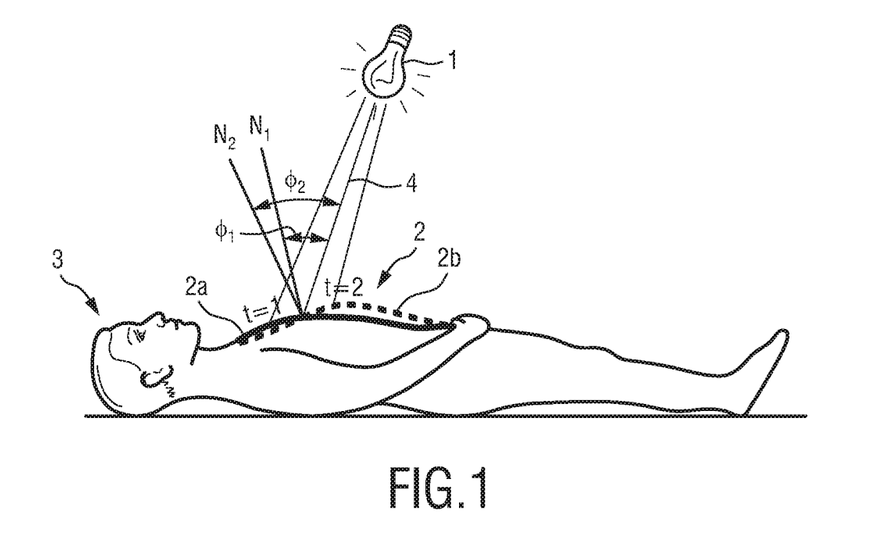
FIG. 1 shows a diagram illustrating illumination of a skin surface at different orientations of the skin surface.

FIG. 1 shows a diagram illustrating illumination of a skin surface at different orientations of the skin surface. A light source 1 with constant location and radiance (W/sr$^{-1}$) provides illumination on skin 2 (in this example the chest wall) of a subject 3 at an angle different from 0° with respect to the normal of the skin. The orientation of the skin 2 varies over time (i.e. between t=1, at which the skin is oriented as indicated by 2a, and t=2, at which the skin is oriented as indicated by 2b) due to heart beat and respiration. This has the effect that the angle φ, defined as the angle of the normal $N_1$ and $N_2$, respectively, with respect to the direction of the illumination 4 varies between $φ_1$ and $φ_2$.

Such changes of the orientation of the skin can, despite motion tracking, significantly impact the PPG signal quality, particularly if the illumination onto the skin is at a large angle with the skin surface-normal. This is because the projected light energy is distributed over a surface, the size of which depends on the angle φ between skin surface-normal and illumination. For illumination from a certain solid angle, the irradiated surface is bigger when the angle between the surface-normal and the incident ray increases, hence the irradiance (W/m$^2$) decreases with increasing angle.

Figure 2A:
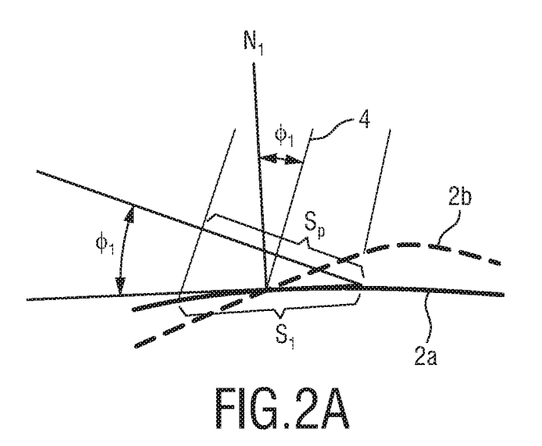
FIG. 2A shows an enlarged portion of the skin surface.
Figure 2B:
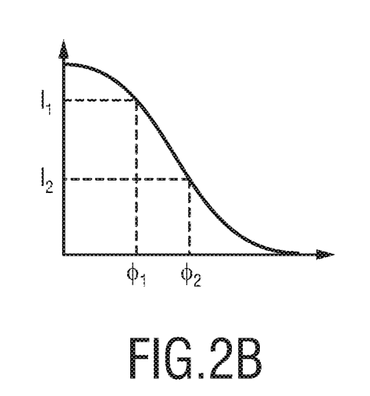
FIG. 2B shows a diagram illustrating the effect of the illumination of a skin surface at different orientations of the skin surface.

This is illustrated in FIG. 2B showing a diagram illustrating the effect of the illumination of a skin surface at different orientations of the skin surface. FIG. 2A shows an enlarged portion of the skin 2 and FIG. 2B shows a diagram of the irradiance I (in W/cm$^2$) over the angle φ. The irradiance of the skin that is illuminated is largest for the surface area $S_p$, perpendicular to the direction of illumination 4. Surface area $S_1$ (at t=1) is larger than the surface area $S_p$ by a factor of $1/\cos(φ_1)$. When the skin orientation changes from $φ_1$ to $φ_2$ the irradiance varies as depicted in FIG. 2B. Hereby, irradiance is expressed as $I(φ)=I_0 \cos(φ)$. Orientation changes in time, φ(t), now translate into irradiance changes in time I(t).

It holds in particular that:

$$S_1=S_p/\cos(φ_1)$$

$$S_2=S_p/\cos(φ_2)$$

$$I_1=(I/S_p)\cos(φ_1)$$

$$I_2=(I/S_p)\cos(φ_2)$$

Figure 3A:
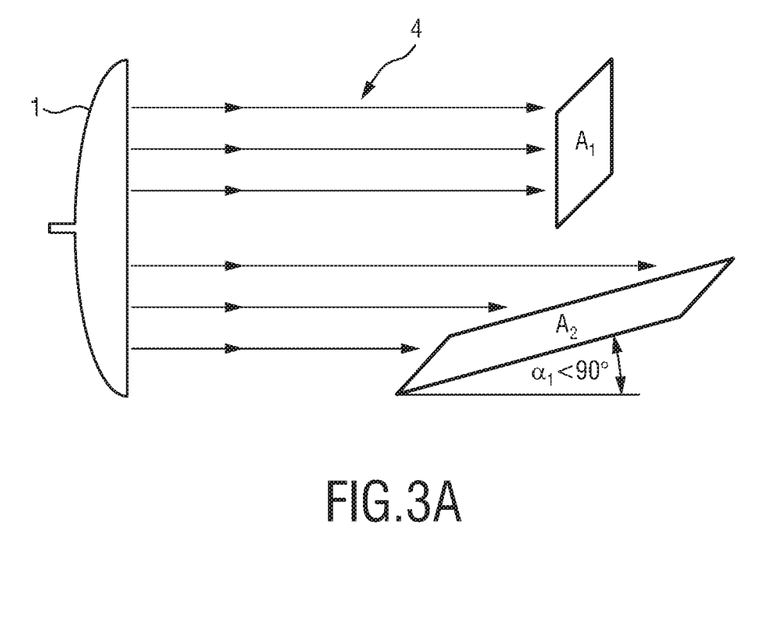
FIGS. 3A and 3B show diagrams illustrating the effect of different skin orientation on pulsatility.
Figure 3B:
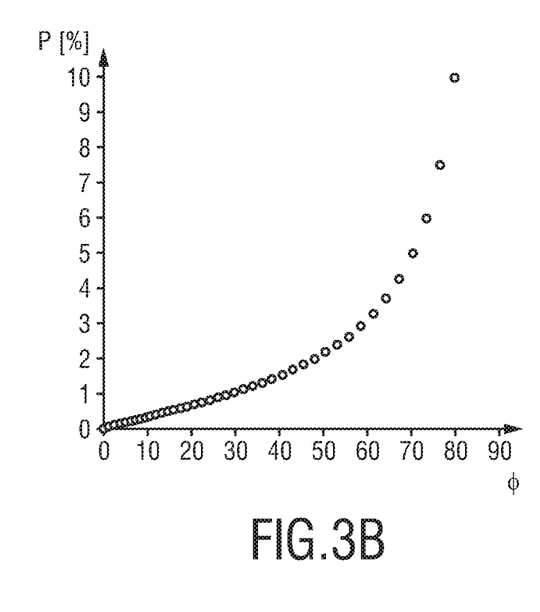

As the irradiance varies as described, also the diffuse radiance (light emitted from the skin) will vary and possibly obfuscate the true PPG signal which is of interest for vital signs measurements such as HR, RR, and SpO2. Assuming a skin surface rotation of 1° with respect to the illumination (i.e. the incident light) caused by e.g. heart beat induced palpations, the reflected light shows pulse-frequent intensity variations, as shown in the diagrams depicted in FIGS. 3A and 3B. Hereby, FIG. 3A shows a diagram illustrating the effect of different skin orientations and FIG. 3B shows a diagram of the relative pulsatility P (in %) over the angle (I). As can be seen, a periodic orientation change over 1° of the skin surface gives a negligible pulsatility of the reflected light for perpendicular illumination, but rapidly increases for angles above 45°. In the upper half of FIG. 3A the surface $R_1$ (also called Lambertian surface) is perpendicular to the incident light (i.e. $α_1=90°$) so that a small area $A_1$ is illuminated with maximum luminance (intensity per unit area). In the lower half of FIG. 3B the surface $R_2$ is arranged at an angle $α_2<90°$ to the incident light so that a larger area $A_2>A_1$ is illuminated with lower luminance.

The present invention minimizes the amplitude of the variation in irradiance by adapting the angle of illumination of the skin. In an embodiment the angle of illumination is controlled such that it is substantially perpendicular to the average skin orientation of a region of interest (ROI), or as close as possible to this perpendicular direction. In another embodiment at least illumination from large angles φ, e.g. larger than 45 degrees are prevented. As a result, the variation in irradiance (noise) due to subject movements will be greatly reduced compared to a system that applies a fixed illumination of the subject. This can be seen in FIG. 4 illustrating the effect of the present invention.

Figure 4:
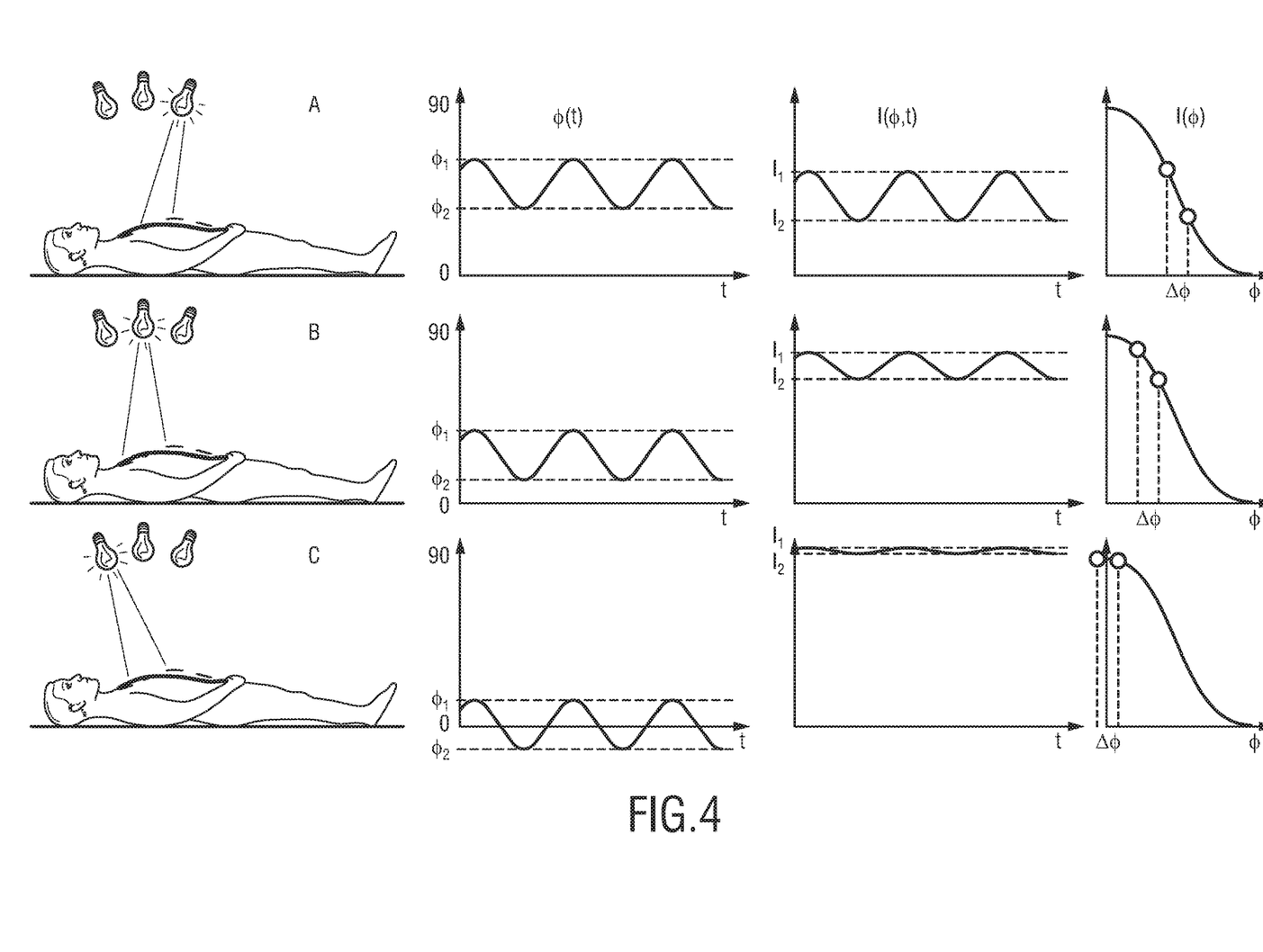
FIG. 4 shows a diagram illustrating the effect of the present invention.

FIG. 4 shows particularly the angle ϕ over time t, the irradiance I over time t and the irradiance I over the angle ϕ, all for three different angles of irradiation (or lamp positions called positions A, B and C). At lamp position A, the irradiance is highly periodic due to the periodic changes in skin orientation. At position B, the periodicity in irradiance is somewhat mitigated, i.e. the temporal variation is smaller and the overall irradiance level is higher than at position A. At lamp position C, the impact of the skin orientation is minimized. Further, the variation in irradiance is strongly diminished and, in addition, the frequency has doubled.

Figure 5:
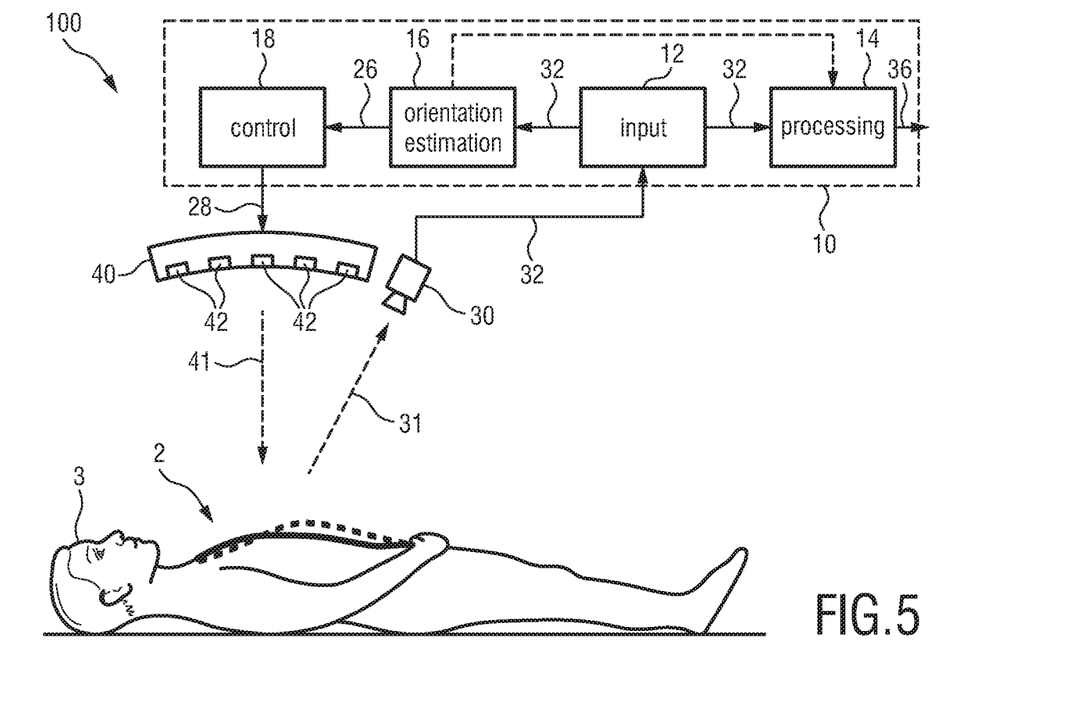
FIG. 5 shows a schematic diagram of a first embodiment of a system according to the present invention.

FIG. 5 shows a schematic diagram of a first embodiment of a system 100 for obtaining vital sign related information of a living being 3 according to the present invention. The system 100 comprises a detection unit 30, e.g. a camera, for receiving light 31 in at least one wavelength interval reflected from a skin region 2 (e.g. here the chest wall; other areas may be a hand, an arm, the belly area, the forehead, the check, etc.) of a living being 3 and for generating an input signal 32 from the received light 31 representing vital sign related information from which a vital sign of the living being can be derived. An illumination unit 40, e.g. comprising two or more light sources (e.g. LEDs) 42 illuminates said skin region 2 with light 41. An orientation estimation unit 16 estimates the orientation 26 of said skin region 2, for which step various options exist as will be explained below in more detail. A control unit 18 controls said illumination unit 40 by a control signal 28 based on the estimated orientation 26 of said skin region 2.

The orientation estimation unit 16 and the control unit 18 may be part of a separate device 10, which, in this embodiment, comprises an input unit 12, e.g. a signal interface, for receiving the input signals 32 from the detection unit 30. Further, the device 10 may comprise a processing unit 14 for processing the input signal 32 and deriving vital sign information 36 of said living being 3 from said input signal 32, preferably by use of photoplethysmography.

One or more units of the device 10 may also be comprised in one or multiple digital or analog processors depending on how and where the invention is applied. The different units may completely or partly be implemented in software and carried out on a personal computer connected to one or more detectors. Some or all of the required functionality may also be implemented in hardware, e.g. in an application specific integrated circuit (ASIC) or in a field programmable gate array (FPGA).

A system 100 as illustrated in FIG. 5 may, e.g., be located in a hospital, healthcare facility, elderly care facility or the like. Apart from the monitoring of patients, the present invention may also be applied in other fields such as neonate monitoring, general surveillance applications, security monitoring or so-called live style environments, such as fitness equipment, or the like. The uni- or bidirectional communication between the device 10, the detection unit 30 and the illumination unit 40 may work via a wireless or wired communication. Other embodiments of the present invention may include a device 10, which is not provided as a stand-alone device, but one or more elements of the device 10, e.g. the orientation estimation unit 16 and the control unit 18, may be integrated into the detection unit 30 or the illumination unit, and the processing unit 14 may be integrated into another device, such as a workstation at a nurse station or integrated into a hospital network.

Generally, the interaction of electromagnetic radiation, in particular light, with biological tissue is complex and includes the (optical) processes of (multiple) scattering, backscattering, absorption, transmission and (diffuse) reflection. The term "reflect" as used in the context of the present invention is not to be construed as limited to specular reflection but comprises the afore-mentioned types of interaction of electromagnetic radiation, in particular light, with tissue and any combinations thereof.

The term "vital sign" as used in the context of the present invention refers to a physiological parameter of a subject (i.e. a living being) and derivative parameters. In particular, the term "vital sign" comprises blood volume pulse signal, heart rate (HR) (sometimes also called pulse rate), heart rate variability (pulse rate variability), pulsatility strength, perfusion, perfusion indicator, perfusion variability, Traube Hering Mayer waves, respiratory rate (RR), skin temperature, blood pressure, a concentration of a substance in blood and/or tissue, such as (arterial) blood oxygen saturation or glucose level. Furthermore, "vital sign" generally includes health indications obtained from the shape of the PPG signal (e.g. shape may say something about partial arterial blockage (e.g. shape obtained from PPG signals of the hand gets more sinusoidal when applying a blood-pressure cuff on the arm), or about the skin thickness (e.g. a PPG signal from the face is different than from the hand), or maybe even about the temperature, etc.).

The term "vital sign related information" as used in the context of the present invention comprises information, from which one or more vital signs as defined above can be derived. Furthermore, it comprises data referring to a physiological parameter, corresponding waveform traces or data referring to a physiological parameter of a time that can serve for subsequent analysis.

In the embodiment shown in FIG. 5 the detection unit 30 comprises a camera (also referred to as imaging unit, or as camera-based or remote PPG sensor) including a suitable photosensor for (remotely and unobtrusively) capturing image frames of the subject 3 (at least of the skin region 2, in particular for acquiring a sequence of image frames over time, from which photoplethysmography signals can be derived. The image frames captured by the camera may particularly correspond to a video sequence captured by means of an analog or digital photo-sensor, e.g. in a (digital) camera. Such a camera usually includes a photo-sensor, such as a CMOS or CCD sensor, which may also operate in a specific spectral range (visible, IR) or provide information for different spectral ranges. The camera may provide an analog or digital signal. The image frames include a plurality of image pixels having associated pixel values. Particularly, the image frames include pixels representing light intensity values captured with different photosensitive elements of a photo-sensor. These photosensitive elements may be sensitive in a specific spectral range (i.e. representing a specific color). The image frames include at least some image pixels being representative of a skin portion of the subject. Thereby, an image pixel may correspond to one photosensitive element of a photo-detector and its (analog or digital) output or may be determined based on a combination (e.g. through binning) of a plurality of the photosensitive elements. For obtaining a vital sign information signal of the subject the data signals of skin pixel areas within the skin area are evaluated. Here, a "skin pixel area" means an area comprising one skin pixel or a group of adjacent skin pixels, i.e. a data signal may be derived for a single pixel or a group of skin pixels.

The illumination unit 40 in this embodiment comprises at least two illumination elements 42, i.e. light sources such as LEDs or other light emitting elements. In an exemplary implementation, the orientation estimation unit 16 determines which of these at least illumination elements 42 emits its light closest along the skin-surface-normal (or closest to the surface-normal of the largest part of the skin-surface should the skin surface not be flat). Once this illumination element has been established, the other illumination elements are e.g. dimmed or switched off completely so that the movement induced signals reflected from the skin are minimized in the input signal 32 (and in a PPG signal derived therefrom) conveyed in the light 31 (diffusely) reflected from the skin.

In an embodiment, the image data acquired by the camera representing the detection unit 30 in the system 100 may be used to determine (sequentially) which of the illumination elements 42 radiates closest along the surface-normal of the skin. Approximating the skin as a diffuse or, ideally, as a Lambertian reflector, the illumination element that produces the highest illumination, as measured by the camera and evaluated by the orientation estimation unit 16, is assumed best for that (portion of) skin (and, optionally, used for the actual vital signs determination in the optional processing unit 14, for which purpose the orientation estimation unit 16 informs the processing unit 14 accordingly). After a significant movement of the subject 3, at regular or irregular intervals or even continuously, these steps, representing a kind of calibration, may be repeated to adaptively control the illumination, in particular the angle of illumination of the skin region 2.

The illumination unit 40 may generally be configured as a one- or two-dimensional array of illumination elements 42. The illumination elements 42 may be arranged at a flat or slightly curved frame. Preferably, the illumination elements 42 can be individually controlled.

Generally, the control unit 18 is configured to control the intensity, direction, distribution, and/or illumination angle of the light emitted by the illumination unit 40.

Figure 6:
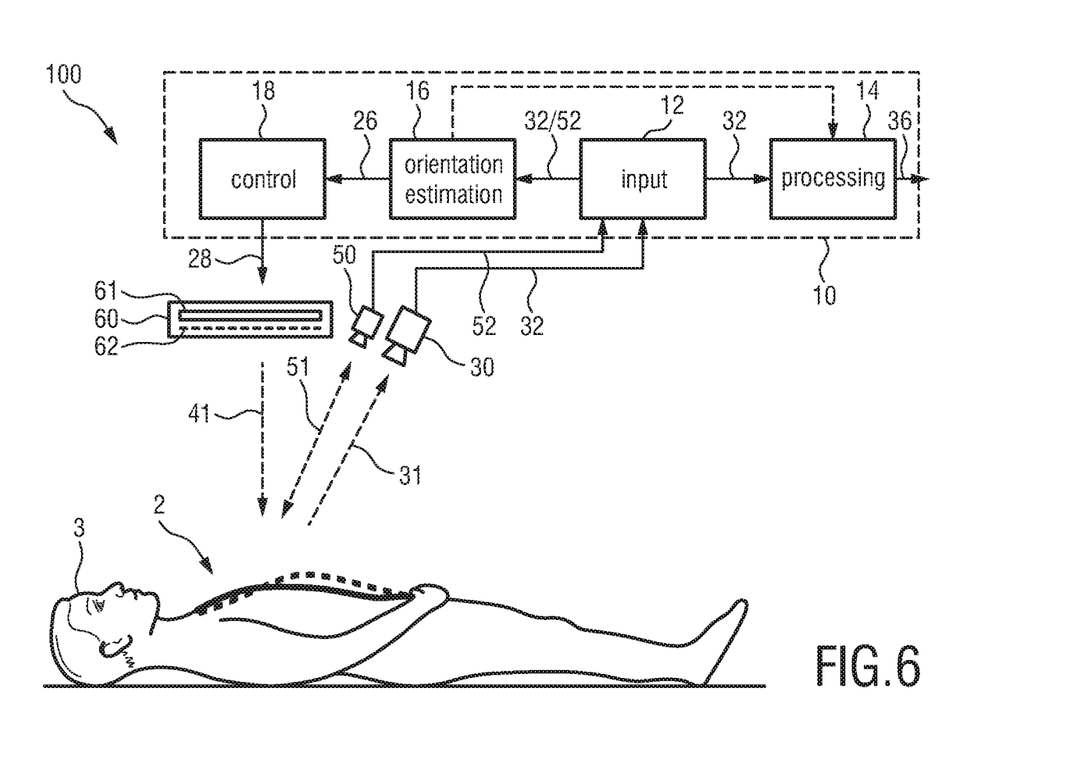
FIG. 6 shows a schematic diagram of a second embodiment of a system according to the present invention.

FIG. 6 shows a schematic diagram of a second embodiment of a system 101 according to the present invention. In this embodiment an additional distance data acquisition unit 50 is provided to acquire distance data 52 representing the distance between the distance data acquisition unit 50 and the skin region 2 by use of radiation 51 emitted to and reflected back from the subject. The distance data acquisition unit 50 may e.g. be a time-of-flight (TOF) camera or a radar unit. From the acquired distance data 52 the orientation estimation unit 16 can determine the orientation of the skin surface of the skin region 2 or can generate a 3D model of the skin surface of the skin region 2. This provides another simple option to estimate the orientation of the skin region in a rather precise manner. However, other methods to establish the 3D model may be employed in other embodiments.

Further, in this embodiment another implementation of an illumination unit 60 is depicted. Said illumination unit 60 comprises a single illumination element 61 and a shutter element 62 comprising (mechanically or electronically) switchable shutters for allowing or preventing the passage of light from different areas of the illumination element 61. For instance, an LCD may be used as illumination element 61 together with an array of individually controllable shutters (i.e. controlled by the control signal 26) between the light emitting element 61 and the subject 3.

Such an illumination unit 60 can also be used in other embodiments of the proposed system, e.g. the system 101 shown in FIG. 5, and an illumination unit 40 can also be used in the embodiment of system 101 shown in FIG. 6.

In a further embodiment, used e.g. with the elements of the system 100 shown in FIG. 5, it may be assumed that the skin is not an ideal Lambertian reflector, i.e. also produces specular reflection or reflectance not along the Lambertian 'cosine law'. This model can particularly be useful if shorter wavelengths are used for which the diffuse reflection can be quite absorbed. In this case the camera can see the highest luminance from the illumination element for which the incident angle equals the camera angle (maximum specular reflection). With a constant camera position it is subsequently possible to determine the position of the illumination element that irradiates mostly along the surface-normal.

In yet another embodiment two neighboring illumination elements 42 of the plurality of illumination elements 42 of the illumination unit 40 (e.g. an LED array) are alternatingly emitting light of equal strength (but under a slightly different angle to the surface-normal). Pairs of illumination elements 42 at different location in the illumination unit 40 alternate at different frequencies. The light 31 reflected from the skin 2 now shows all different frequency components, in particular all different frequency components, but the illumination elements 42 that emit closest to the surface-normal will give the lowest frequency amplitude. Consequently from the (modulation) spectrum of the reflected light 31 it can be determined, which orientation of an illumination element 42 is closest to the surface-normal.

In still another embodiment the spectrum may be measured with the camera pointed at the skin region 2, but higher modulation frequencies are likely possible with a photodiode to which the skin-reflected light is focused. A further alternative is to run the camera at a higher speed (often possible at a lower resolution, the so-called "binning" option of the camera).

Figure 7:
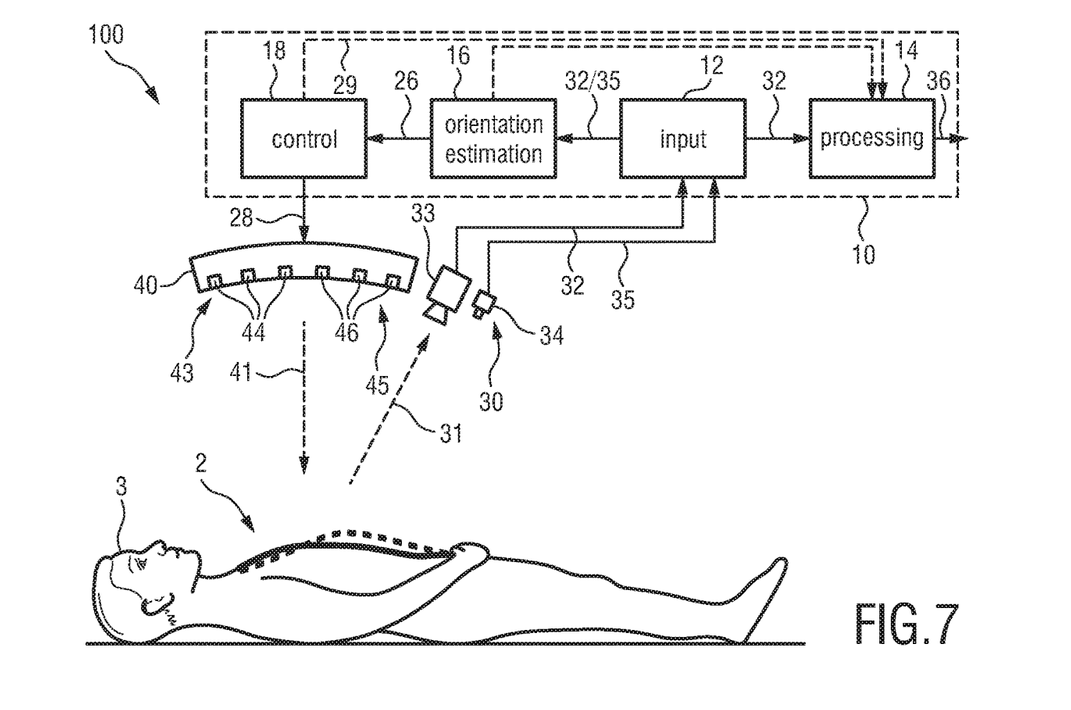
FIG. 7 shows a schematic diagram of a third embodiment of a system according to the present invention.

FIG. 7 shows a schematic diagram of a third embodiment of a system 102 according to the present invention. In this embodiment the detection unit 30 comprises a camera 33 for generating said input signal 32 from light 31 received by the camera 33 and a photodiode 34 for generating reflection signals 35 from light 31 received by the photodiode 34. Further, the illumination unit 40 comprises a first set 43 of illumination elements 44 for illuminating said skin region 2 to enable the generation of input signals 31 by said camera 33 and a second set 45 of illumination elements 46 for illuminating said skin region 2 to enable the generation of reflection signals 35 by said photodiode 34.

Preferably, the wavelengths used by the first set 43 of illumination elements 44 and by the second set 45 of illumination elements 46 differ, i.e. the illumination elements 46 are configured to illuminate said skin region 2 with light of a wavelength or wavelength range outside the sensitivity interval of said camera 33. Further, the number of illumination elements 44 and illumination elements 46 may differ.

Two neighboring illumination elements may also be separated through other means than modulation frequencies, such as the use of slightly different wavelengths, sequential illumination, synchronized flickering at the same frequency, etc.

In the above explained embodiments the control unit 18 controls the illumination unit 40 based on the estimated orientation of the skin region 2. In other embodiments the control unit 18 may, additionally or alternatively, control the processing unit 14 based on the estimated orientation of the skin region 2. In particular, when the illumination unit 40 illuminate the skin region 2 in subsequent time intervals from different illumination angles, the processing unit 14 may be controlled to derive vital sign related information 36 from the input signal obtained during time intervals selected based on the estimated orientation of said skin region, i.e. during time intervals during which the skin region is optimally illuminated. This is illustrated in FIG. 7 by the control signal 29 from the control unit 18 to the processing unit 14, but may also be provided in other embodiments.

For instance, in an implementation only input signals 32 obtained during time intervals, during which the illumination element, whose illumination resulted in the reflection signal with the highest intensity, illuminates said skin region 2 exclusively or with the highest intensity among all illumination elements may be used by the processing unit 14. In another implementation only input signals 32 obtained during time intervals, during which the pair of illumination elements, whose illumination resulted in the reflection signal with the smallest intensity modulation, illuminates said skin region 2 exclusively or with the highest intensity among all illumination elements may be used by the processing unit 14. Hence, in such embodiments the illumination unit may illuminate the skin region 2 continuously in the same manner, optionally without additional control.

Figure 8:
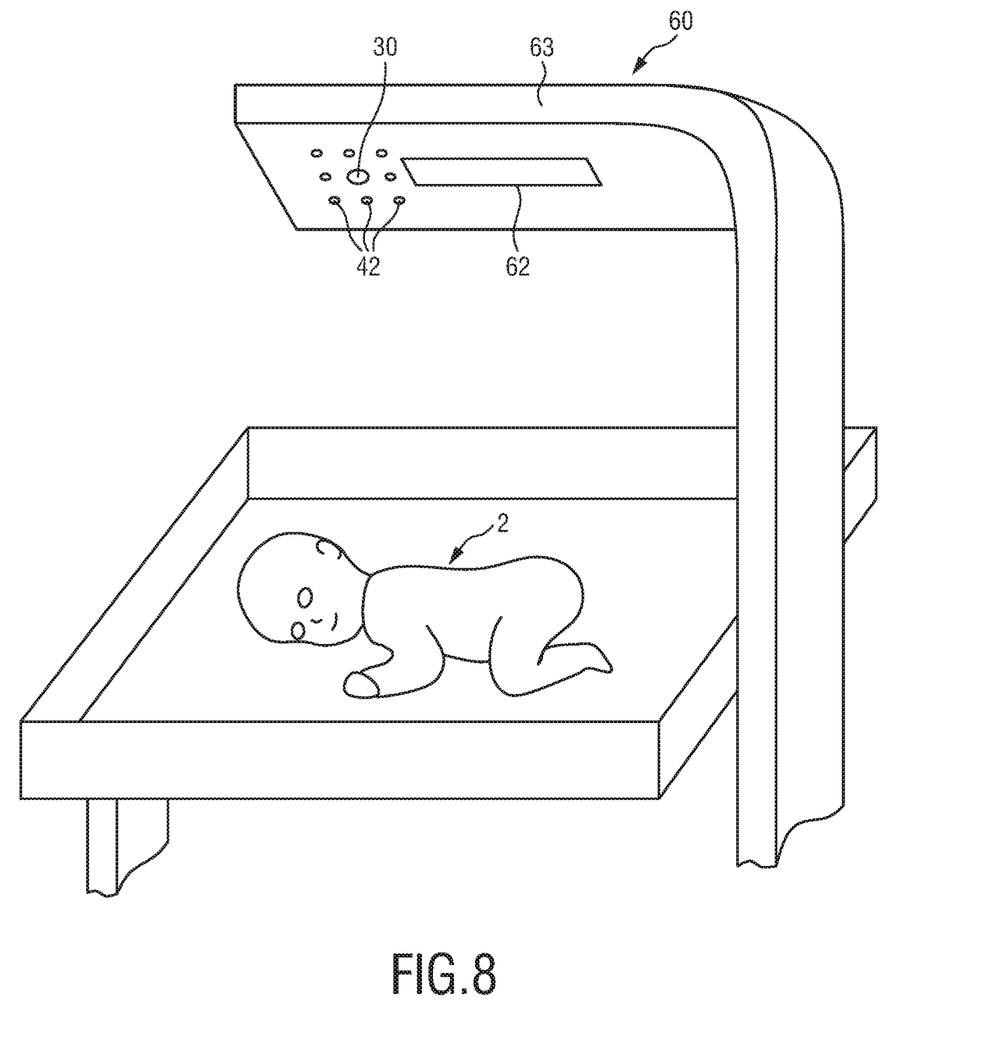
FIG. 8 shows a schematic diagram of a fourth embodiment of a system according to the present invention.

FIG. 8 shows a schematic diagram of a fourth embodiment of a system 103 according to the present invention, wherein the elements of the device 10 are not explicitly shown. In this embodiment the illumination unit and the detection unit are embedded into a radiant warmer 60. Babies are often kept in such a radiant warmer 60 to help keeping the temperature of the baby regulated. This gives better access to the baby for treatment, care and procedures.

A radiant warmer 60 normally has an IR warming lamp 62 centered above the baby 2. The means to hold the heating element 62 makes it also the ideal place to integrate the detection unit 30, here in the form of a camera as explained above, frontend along with this heating element 62 at the same spot as much as space allows. The arm 63 that carries the heating element 62 can also carry the camera 30 inside (basically invisible as it only need a little hole). Further, the arm contain the illumination elements 42 of the illumination unit 40, here in the form of an array around the camera 30. Cable routing can be managed there perfectly inside the warmer 60, in particular the arm 63. The device 10 may also be integrated in the radiant warmer 60. Further, the radiant warmer 60 may share a user interface and any further potential computation means that may be required for the monitoring and the warming functions. In a similar way some or all elements of the proposed system may be integrated into an incubator.

Figure 9:
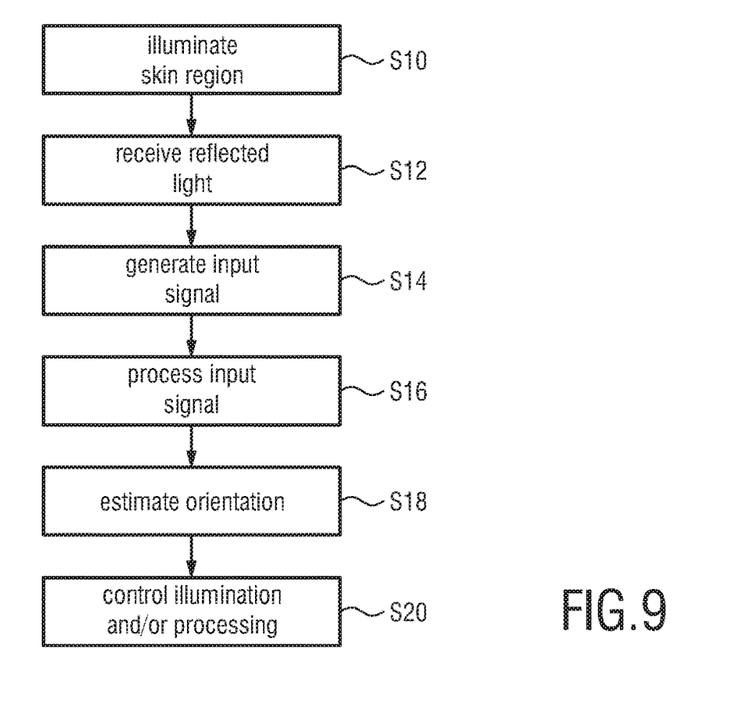
FIG. 9 shows an embodiment of a method according to the present invention.

A flowchart of an embodiment of a method according to the present invention is shown in FIG. 9. In a first step S10 at least a skin region 2 of a living being 3 is illuminated with light. In a second step S12 light 31 in at least one wavelength interval reflected from said skin region 2 is received. In a third step S14 an input signal 32 is generated from the received light 31 representing vital sign related information from which a vital sign of the living being can be derived. In a fourth step S16 the input signal 32 is processed to derive vital sign information 36 of said living being from said input signal 32. In a fifth step S18 the orientation of said skin region 2 is estimated. In a sixth step S18 said illumination unit 40 based on the estimated orientation of said skin region 2 to illuminate said skin region 2 and/or said processing to derive vital sign related information 36 based on the estimated orientation of said skin region.

In summary, vital signs measurement devices derive vital sign information by measuring the subtle change in the skin area of the region of interest, which in turn relies on the illumination. Normally, a dedicated illumination is needed. However, it has been found that one particular pre-set illumination might not always be optimal for measurement. For example, specular reflection is one of the difficulties, in particular for SpO2 measurement, which should be avoided in the region of interest (ROI) used for measurement. Due to different skin types (conditions) and body postures or after body movement, specular reflections might exist or appear in the ROI. Manually adjusting illumination setup for each measurement, or after each change in the environment or the vital signs measurement device, is subjective and time consuming.

Hence, the present invention proposes an adaptive device and method for unobtrusive vital signs measurement (e.g. heartbeat monitoring, SpO2 monitoring, etc.), which can be automatically configured for optimal measurement. Accordingly, a control unit is provided that controls said illumination unit, e.g. one or more controllable light sources, and/or the processing unit for deriving vital signs related information, e.g. a vital sign itself or a signal from which a vital sign can be derived, based on the estimated orientation of the skin surface. Thus, even in case of changing conditions vital sign related information can be obtained with optimal accuracy and reliability.

The present invention may be applied in various applications. Heart rate, respiration rate, and SpO2 are very relevant factors in patient monitoring and home-healthcare where remote heart rate monitoring becomes more and more relevant. Further, the present invention may be applied to register heartbeat in fitness devices. The proposed invention can particularly be applied in any application where (contactless) camera-based vital signs monitoring is performed with controllable illumination that is changing or with variable light conditions. Typical application areas are e.g. premature babies with very sensitive skin in NICUs and patients with damaged (e.g. burns) skin. Locations of application include NICU, emergency waiting room, general ward, nursing homes, home healthcare, and psychiatric ward/prison. Normally, the vital signs extraction is extremely challenging and even impossible in some cases, but can now be accurately and reliably achieved. Further, the present invention can be applied in contact PPG device, such as contact pulse oximeters or fingerclip sensors for SpO2 measurement.

Furthermore, the different embodiments can take the form of a computer program product accessible from a computer usable or computer readable medium providing program code for use by or in connection with a computer or any device or system that executes instructions. For the purposes of this disclosure, a computer usable or computer readable medium can generally be any tangible device or apparatus that can contain, store, communicate, propagate, or transport the program for use by or in connection with the instruction execution device.

In so far as embodiments of the disclosure have been described as being implemented, at least in part, by software-controlled data processing devices, it will be appreciated that a non-transitory machine-readable medium carrying such software, such as an optical disk, a magnetic disk, semiconductor memory or the like, is also considered to represent an embodiment of the present disclosure.

The computer usable or computer readable medium can be, for example, without limitation, an electronic, magnetic, optical, electromagnetic, infrared, or semiconductor system, or a propagation medium. Non-limiting examples of a computer readable medium include a semiconductor or solid state memory, magnetic tape, a removable computer diskette, a random access memory (RAM), a read-only memory (ROM), a rigid magnetic disk, and an optical disk. Optical disks may include compact disk—read only memory (CD-ROM), compact disk—read/write (CD-R/W), and DVD.

Further, a computer usable or computer readable medium may contain or store a computer readable or usable program code such that when the computer readable or usable program code is executed on a computer, the execution of this computer readable or usable program code causes the computer to transmit another computer readable or usable program code over a communications link. This communications link may use a medium that is, for example, without limitation, physical or wireless.

A data processing system or device suitable for storing and/or executing computer readable or computer usable program code will include one or more processors coupled directly or indirectly to memory elements through a communications fabric, such as a system bus. The memory elements may include local memory employed during actual execution of the program code, bulk storage, and cache memories, which provide temporary storage of at least some computer readable or computer usable program code to reduce the number of times code may be retrieved from bulk storage during execution of the code. Input/output, or I/O devices, can be coupled to the system either directly or through intervening I/O controllers. These devices may include, for example, without limitation, keyboards, touch screen displays, and pointing devices. Different communications adapters may also be coupled to the system to enable the data processing system to become coupled to other data processing systems, remote printers, or storage devices through intervening private or public networks. Non-limiting examples are modems and network adapters and are just a few of the currently available types of communications adapters.

The description of the different illustrative embodiments has been presented for purposes of illustration and description and is not intended to be exhaustive or limited to the embodiments in the form disclosed. Many modifications and variations will be apparent to those of ordinary skill in the art. Further, different illustrative embodiments may provide different advantages as compared to other illustrative embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

The invention claimed is:

1. A device for obtaining vital sign related information of a living being, said device comprising:
    an input configured to receive an input signal generated from light received in at least one wavelength interval reflected from a skin region of the living being, said input signal representing vital sign related information from which a vital sign of the living being can be derived;
    a processor configured to process the input signal and to derive vital sign related information of said living being from said input signal;
    an orientation estimator configured to estimate the orientation of said skin region, wherein said orientation estimator is configured to process distance data to determine a 3D model of the skin surface including said skin region from said distance data; and
    a controller configured to control an illuminator configured to illuminate said skin region with light to illuminate said skin region based on an estimated orientation of said skin region and/or to control said processor to derive vital sign related information from said input signal during time intervals selected based on the estimated orientation of said skin region.

2. The device as claimed in claim 1, wherein said controller is configured to control the intensity, direction, distribution, and/or illumination angle of at least part of the light emitted by said illuminator.

3. The device as claimed in claim 1,
    wherein said orientation estimator is configured to estimate the orientation of the surface-normal of said skin region; and
    wherein said controller is configured to control the intensity, direction, distribution, and/or illumination angle of at least part of the light emitted by said illuminator such that most or all light is emitted from an illumination angle closest or identical to the estimated surface-normal.

4. The device as claimed in claim 1, wherein said controller is configured to control said illuminator to illuminate said skin region in subsequent time intervals from different illumination angles and to control said processor to derive vital sign related information from said input signal obtained during time intervals selected based on the estimated orientation of said skin region.

5. The device as claimed in claim 1, wherein said orientation estimator is configured to regularly or continuously estimate the orientation of said skin region and wherein said controller is configured to adjust the control of the illuminator accordingly.

6. The device as claimed in claim 1, wherein said orientation estimator is further configured to process time-of-flight data.

7. A system for obtaining vital sign related information of a living being, said system comprising:
    a detector configured to receive light in at least one wavelength interval reflected from a skin region of a living being and to generate an input signal from the received light representing vital sign related information from which a vital sign of the living being can be derived;
    an illuminator configured to illuminate said skin region with light; and
    a device as claimed in claim 1 for obtaining vital sign related information of a living being from said input signal.

8. The system as claimed in claim 7, wherein said illuminator comprises two or more illumination elements.

9. The system as claimed in claim 8, wherein said two or more illumination elements are arranged at different locations and/or with different orientations for illuminating a skin region from different illumination angles.

10. The system as claimed in claim 8, wherein said controller is configured to individually control said illumination elements.

11. The system as claimed in claim 10, wherein said controller is configured to individually control the intensity of the illumination elements.

12. The system as claimed in claim 8, wherein;
said controller is configured to control said illumination elements to illuminate said skin region in a multiplexed and/or modulated manner;
said detector is configured to subsequently receive light reflected from said skin region in response to said subsequent illuminations and to generate reflection signals from the received light;
said orientation estimator is configured to determine the reflection signal with the highest intensity; and
said controller is further configured to control said illuminator such that the illumination element, whose illumination resulted in the reflection signal with the highest intensity, illuminates said skin region exclusively or with the highest intensity among all illumination elements and/or to control said processor to derive vital sign related information from said input signal obtained during time intervals, during which the illumination element, whose illumination resulted in the reflection signal with the highest intensity, illuminates said skin region exclusively or with the highest intensity among all illumination elements.

13. The system as claimed in claim 9, wherein;
said controller is configured to control said illumination elements to pairwise illuminate said skin region, wherein different pairs of neighboring illumination elements alternately illuminate said skin region with different alternation frequencies, with different wavelengths, at different times and/or with a synchronized flickering;
said detector is configured to subsequently receive light reflected from said skin region in response to said alternate illuminations and to generate reflection signals from the received light;
said orientation estimator is configured to determine the reflection signal with the smallest intensity modulation; and
said controller is further configured to control said illuminator such that the pair of illumination elements, whose illumination resulted in the reflection signal with the smallest intensity modulation, illuminates said skin region exclusively or with the highest intensity among all illumination elements or such that only illumination in time slots with illumination that resulted in the reflection signal with the smallest intensity modulation is used for illumination of said skin region and/or to control said processor to derive vital sign related information from said input signal obtained during time intervals, during which the pair of illumination elements, whose illumination resulted in the reflection signal with the smallest intensity modulation, illuminates said skin region exclusively or with the highest intensity among all illumination elements.

14. The system as claimed in claim 13,
wherein said detector comprises a camera for generating said input signal from light received by the camera and a photodiode for generating said reflection signals from light received by the photodiode; and
wherein said illuminator comprises a first set of illumination elements for illuminating said skin region to enable the generation of input signals by said camera and a second set of illumination elements for illuminating said skin region to enable the generation of reflection signals by said photodiode.

15. The system as claimed in claim 14, wherein the illumination elements of said second set are configured to illuminate said skin region with light of a wavelength or wavelength range outside the sensitivity interval of said camera.

16. The system as claimed in claim 7, wherein said illuminator comprises a plurality of LEDs.

17. A method for obtaining vital sign information of a living being, comprising:
receiving an input signal generated from light received in at least one wavelength interval reflected from a skin region of a living being, said input signal representing vital sign related information from which a vital sign of the living being can be derived;
processing said input signal and deriving vital sign information of said living being from said input signal;
estimating the orientation of said skin region by:
processing distance data; and
determining a 3D model of the skin surface including said skin region from said distance data; and
controlling illumination of said skin region with light based on said estimated orientation of said skin region and/or said processing to derive vital sign related information from said input signal obtained during time intervals selected based on the estimated orientation of said skin region.

18. A non-transitory computer-readable recording medium that stores therein a computer program product, which, when executed on a processor, causes the method as claimed in claim 17 to be performed.

19. A system for obtaining vital sign related information of a living being, said system comprising a processor configured to carry out the steps of:
receiving an input signal generated from light received in at least one wavelength interval reflected from a skin region of a living being, said input signal representing vital sign related information from which a vital sign of the living being can be derived;
processing said input signal and deriving vital sign information of said living being from said input signal;
estimating the orientation of said skin region by:
processing distance data; and
determining a 3D model of the skin surface including said skin region from said distance data; and
controlling illumination of said skin region with light based on said estimated orientation of said skin region and/or said processing to derive vital sign related information from said input signal obtained during time intervals selected based on the estimated orientation of said skin region.

* * * * *